United States Patent
Richter et al.

(10) Patent No.: US 10,226,337 B2
(45) Date of Patent: *Mar. 12, 2019

(54) METHOD AND APPARATUS FOR FINE ADJUSTMENT OF A PERCUTANEOUS VALVE STRUCTURE

(71) Applicant: Valve Medical Ltd., Tel Aviv (IL)

(72) Inventors: Yoram Richter, Ramat Hasharon (IL); Jacob Richter, Arsuf (IL); Ety Weisz, Tel Aviv (IL)

(73) Assignee: Valve Medical Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,631

(22) Filed: Dec. 17, 2016

(65) Prior Publication Data
US 2017/0095329 A1 Apr. 6, 2017

Related U.S. Application Data

(63) Continuation of application No. 14/638,278, filed on Mar. 4, 2015, now Pat. No. 9,554,896, which is a
(Continued)

(51) Int. Cl.
*A61F 2/06* (2013.01)
*A61F 2/24* (2006.01)

(52) U.S. Cl.
CPC .......... *A61F 2/2418* (2013.01); *A61F 2/2409* (2013.01); *A61F 2/2427* (2013.01);
(Continued)

(58) Field of Classification Search
CPC .... A61F 2/2409; A61F 2/2418; A61F 2/2427; A61F 2250/0006; A61F 2250/0008
See application file for complete search history.

(56) References Cited

U.S. PATENT DOCUMENTS

| | | | |
|---|---|---|---|
| 4,705,516 A | 11/1987 | Barone | |
| 5,411,552 A | 5/1995 | Anderson et al. | |

(Continued)

FOREIGN PATENT DOCUMENTS

| | | |
|---|---|---|
| EA | 023209 B1 | 5/2016 |
| EP | 2 379 010 B1 | 3/2015 |

(Continued)

OTHER PUBLICATIONS

International Search Report and Written Opinion from related international application No. PCT/IB2010/000051, dated Mar. 31, 2010, 14 pages.
(Continued)

*Primary Examiner* — Brian Dukert
(74) *Attorney, Agent, or Firm* — Cadwalader, Wickersham & Taft LLP

(57) ABSTRACT

The invention provides a device for fine adjustment of a prosthetic valve device and a method of adjusting the position of a prosthetic valve after implantation. The adjustment mechanism includes complementary structures on a valve member and device frame that cooperate to provide relative axial and/or angular motion between the valve member and device frame (and thus the native vessel). The adjustment mechanism of the invention may also include a means for selectively maintaining the relative position of the valve member and device frame. The device and method are particularly applicable for use with a modular prosthetic valve device that is assembled in the body lumen.

20 Claims, 6 Drawing Sheets

Related U.S. Application Data continuation of application No. 12/686,340, filed on Jan. 12, 2010, now Pat. No. 8,998,982.

(60) Provisional application No. 61/144,007, filed on Jan. 12, 2009.

(52) U.S. Cl.
CPC .......... *A61F 2230/0013* (2013.01); *A61F 2250/0006* (2013.01); *A61F 2250/006* (2013.01); *A61F 2250/0008* (2013.01)

(56) References Cited

U.S. PATENT DOCUMENTS

| | | | |
|---|---|---|---|
| 5,840,081 | A | 11/1998 | Anderson et al. |
| 6,168,614 | B1 | 1/2001 | Anderson et al. |
| 6,893,460 | B2 | 5/2005 | Spenser et al. |
| 2005/0137686 | A1 | 6/2005 | Salahieh et al. |
| 2005/0137688 | A1 | 6/2005 | Salahieh et al. |
| 2005/0165479 | A1 | 7/2005 | Drews et al. |
| 2005/0283231 | A1 | 12/2005 | Haug et al. |
| 2005/0288780 | A1 | 12/2005 | Rhee et al. |
| 2006/0195180 | A1 | 8/2006 | Kheradvar et al. |
| 2006/0287717 | A1 | 12/2006 | Rowe et al. |
| 2007/0016288 | A1 | 1/2007 | Gurskis et al. |
| 2007/0260305 | A1 | 11/2007 | Drews et al. |
| 2007/0265701 | A1 | 11/2007 | Gurskis et al. |

FOREIGN PATENT DOCUMENTS

| | | |
|---|---|---|
| WO | WO 00/47139 A1 | 8/2000 |
| WO | WO 07/009117 A1 | 1/2007 |
| WO | WO 07/100410 | 9/2007 |
| WO | WO 2010/079426 | 7/2010 |

OTHER PUBLICATIONS

Singh, I.M. et al., "Percutaneous Treatment of Aortic Valve Stenosis," Cleve. Clinc. J. Med. 75 (11): 805-812 (Nov. 2008).

Piazza, N. et al., "Early and Persistent Intraventricular Conduction Abnormalities and Requirements for Pacemaking after Percutaneous Replacement of the Aortic Valve," JACC Cardiovascular Interventions 1(3): 310-316 (2008).

Piazza, N. et al., "Anatomy of the Aortic Valvar Complex and its Implications for Transcatheter Implantation of the Aortic Valve," Circ. Cardiovasc. Interventions 1: 74-81 (2008).

Zegdi, R., et al., "A Repositionable Valved Stent for Endovascular Treatment of Deteriorated Bioprostheses," J.Am. Coll. Cardiol. 48(7): 1365-1368 (2006).

Webb, J.G. et al., "Percutaneous Aortic Valve Implantation Retrograde from the Femoral Artery," Circulation 113: 842-850 (2006).

Ussia, G.P. et al., "The Valve-in-Valve Technique: Transcatheter Treatment of Aortic Bioprosthesis Malposition," Cath. Cardiovasc. Interventions 73: 713-716 (2009).

Lutter, G. et al., "Percutaneous Valve Replacement: Current State and Future Prospects," Ann. Thorac. Surg. 78: 2199-2206 (2004).

Ghanbari, H. et al., "Percutaneous Heart Valve Replacement: An Update," ETCMED 18(4): 1050-1738.

Buellesfeld, L. et al., "Percutaneous Implantation of the First Repositionable Aortic Valve Prosthesis in a Patient with Severe Aortic Stenosis," Cath. Cardio. Interventions 71: 579-584 (2008).

Webb, J.G. et al., "Percutaneous Suture Edge-to-Edge Repair of the Mitral Valve," EuroIntervention 5: 86-89(2009).

Office actions and responses of related U.S. Appl. No. 12/686,340, now U.S. Pat. No. 8,998,982: Notice of Allowance dated Dec. 5, 2014; Response to Advisory Action with Request for Continued Examination dated Nov. 14, 2014; Advisory Action dated Oct. 22, 2014; Amendment and Response to Final Rejection dated Oct. 14, 2014; Final Rejection dated Aug. 15, 2014; Response to Non-Final Rejection dated May 14, 2014; Non-Final Rejection dated Feb. 14, 2014; Amendment and Response to Final Rejection with Request for Continued Examination dated Dec. 27, 2013; Final Rejection dated Nov. 7, 2013; Amendment and Response to Non-Final Rejection dated Aug. 13, 2013; Non-Final Rejection dated May 17, 2013; Amendment and Response to Advisory Action with Request for Continued Examination dated Mar. 8, 2013; Advisory Action dated Feb. 1, 2013; Amendment and Argument after Notice of Appeal; and Notice of Appeal filed Jan. 9, 2013; Final Rejection dated Oct. 12, 2012; Amendment and Response to Non-Final Rejection dated Jul. 12, 2012; and Non-Final Rejection dated Apr. 23, 2012.

Office actions and responses of related U.S. Appl. No. 14/638,278, now U.S. Pat. No. 9,554,896: Notice of Allowance dated Sep. 26, 2016; Amendment and Response to Final Rejection with Request for Continued Examination (RCE) dated Sep. 14, 2016; Advisory Action and After Final Consideration Program Decision dated Aug. 29, 2016; Amendment and Response to Final Rejection with After Final Consideration Program Request dated Aug. 18, 2016; Final Rejection dated Jul. 8, 2016; Terminal Disclaimer Review Decision dated Apr. 27, 2016; Amendment and Response to Non-Final Rejection with Terminal Disclaimer dated Apr. 11, 2016; Non-Final Rejection dated Jan. 11, 2016; and Preliminary Amendment dated Mar. 4, 2015.

U.S. Appl. No. 61/144,007, filed Jan. 12, 2009, Richter et al.

METHOD AND APPARATUS FOR FINE ADJUSTMENT OF A PERCUTANEOUS VALVE STRUCTURE

This application is a continuation of U.S. patent application Ser. No. 14/638,278, filed Mar. 4, 2015, which is a continuation of U.S. patent application Ser. No. 12/686,340, filed Jan. 12, 2010, issued as U.S. Pat. No. 8,998,982 on Apr. 7, 2015 and claims the benefit of priority of U.S. Provisional Application Ser. No. 61/144,007, filed Jan. 12, 2009, all of which are incorporated herein by reference in their entirety.

FIELD OF THE INVENTION

The present invention relates to an adjustment mechanism for finely adjusting the position of a percutaneous prosthetic valve devices. The invention further relates to a method of positioning a percutaneous prosthetic valve in a target location of a body lumen with enhanced accuracy. The apparatus and method of the invention are applicable to pre-assembled valve devices or modular valve devices, i.e., a prosthetic valve capable of being delivered in parts and assembled in the body.

BACKGROUND OF THE INVENTION

The human body contains a wide variety of natural valves, such as, for example, heart valves, esophageal and stomach valves, intestinal valves, and valves within the lymphatic system. Natural valves may degenerate for a variety of reasons, such as disease, age, and the like. A malfunctioning valve fails to maintain the bodily fluid flow in a single direction with minimal pressure loss. An example of a malfunctioning valve is a heart valve that may be either stenotic, i.e., the leaflets of the valve do not open fully, or regurgitant, i.e., the leaflets of the valve do not close properly. It is desirable to restore valve function to regain the proper functioning of the organ with which the valve is associated. For example, proper valve function in the heart ensures that blood flow is maintained in a single direction through a valve with minimal pressure loss, so that blood circulation and pressure can be maintained. Similarly, proper esophageal valve function ensures that acidic gastric secretions do not irritate or permanently damage the esophageal lining.

Several percutaneous prosthetic valve systems have been described. One example described in Andersen, et. al. (U.S. Pat. No. 5,411,552) comprises an expandable stent and a collapsible valve which is mounted onto the stent prior to deployment. Spenser, et. al. (U.S. Pat. No. 6,893,460) describe another prosthetic valve device comprising a valve structure made of biological or synthetic material and a supporting structure, such as a stent. The Spenser prosthetic valve is a crimpable leafed-valve assembly consisting of a conduit having an inlet and an outlet, made of pliant material arranged to present collapsible walls at the outlet. The valve assembly is affixed to the support stent prior to deployment. The complete valve device is deployed at a target location within the body duct using a deploying means, such as a balloon catheter or a similar device. Percutaneous implantation of medical devices, particularly prosthetic valves, is a preferred procedure because it allows implantation without the need for opening a large portion of the chest.

Accurate placement of current percutaneous valve devices relative to the existing native anatomy is often problematic, particularly in the case of aortic valve replacements. Consequences of poor valve placement in the case of an aortic valve include functional and/or physical occlusion of the orifice of the coronary artery distal to the aortic valve, and/or increased pressure on and disruption of the electrical conduction apparatus of the heart. Specifically, a prosthetic valve that is placed too distally (i.e., toward the aorta) can occlude or impede flow into the orifices of the coronary arteries. For example, depending on the position of the coronary ostia, either the skirt of the prosthetic valve or large native valve leaflets pressed down against the aorta wall may physically or functionally obstruct the orifices and impede coronary arterial flow. See, e.g., Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008); Webb, J G, et al., "Percutaneous aortic valve implantation retrograde from the femoral artery," CIRCULATION, 113:842-850 (2006). This obstruction may be either physical or it may be functional, i.e., the orifices of the coronary arteries are physically patent, but due to alterations in flow patterns produced by the prosthetic valve, flow into the coronary arteries is partially impeded. A prosthetic valve that is placed too proximally (i.e., toward the ventricular outflow tracts of the left ventricle) can interfere with the anterior leaflet of the Mitral valve, the atrioventricular node or the bundle of His (conduction tissues). Approximately thirty percent of patients receiving prosthetic valves percutaneously require pacemakers, because the valve is placed with the ventricular end too close to or on top of the left bundle branch, putting pressure on the electrical conduction apparatus. See, e.g., Piazza, N., et al., "Early and persistent intraventricular conduction abnormalities and requirements for pacemaking following percutaneous replacement of the aortic valve," JACC CARDIOVASCULARINTERVENTIONS, 1:310-316 (2008); Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008).

Persons of skill in the art recognize that one limitation on percutaneous prosthetic aortic valve replacement methods using currently available pre-assembled valve devices is a less than desirable level of precision for positioning the valve. See Ussia, G. P., et al., The "Valve-in-Valve Technique: Transcatheter Treatment of Aortic Bioprosthesis Malposition," CATHETERIZATION CARDIOVASCULAR INTERVENTIONS, 73:713-716 (2009); Ghanbari, H., et al., "Percutaneous Heart Valve Replacement: An Update," TRENDS CARDIOVASCULAR MEDICINE, 18:117-125, (2008); Lutter, G., et al., "Percutaneous Valve Replacement: Current State and Future Prospects," ANNALS THORACIC SURGERY, 78:2199-2206 (2004).

Repositioning methods have been proposed. Such methods involve a repositioning of the entire valve device rather than adjustment from the previous position. One method of repositioning a percutaneous prosthetic valve involves compressing or relaxing the stent that serves as the frame for the valve. See Zegdi, R. et al., "A Repositionable Valve Stent for Endovascular Treatment of Deteriorated Bioprostheses," J. AMERICAN COLLEGE CARDIOLOGY, 48(7):1365-1368 (2006). Such a method provides little if any fine control over the axial position or angular position of the valve, and risks significant shifting of the entire device and/or damage to the tissue. Another method of repositioning a percutaneous prosthetic valve involves preventing the stent from fully expanding until it is in position, or unexpanding the stent slightly in order to reposition it. Buellesfeld, et al., "Percutaneous Implantation of the First Repositionable Aortic Valve Prosthesis in a Patient with Severe Aortic Stenosis," CATHETERIZATION CARDIOVASCULAR INTERVENTIONS, 71:579-584

(2008); US Published Application No. 2005/0137688A1 to Salahieh et al. Such a method provides little if any fine control over the axial position or angular position of the valve, and repeated expansion and compression of the stent at or near the site of implantation risks damage to the tissue.

Therefore, there is a need in the art for an apparatus and method for making fine adjustments to a valve's position after implantation—i.e., to move the valve in small increments until the proper position is achieved. This adjustment method provides an iterative feedback process where each adjustment is an incremental improvement over the last position. A need also exists for a method of delivering a prosthetic valve with increased safety, e.g., with minimal damage to the vessel wall and with good control of the adjustment process. A device that can be placed in the vessel without incurring further damage to the wall of the body lumen during delivery and/or during adjustment of the valve position—e.g., adjusting the valve, not the frame—is highly desirable.

SUMMARY OF THE INVENTION

It is an object of the invention to provide a percutaneous prosthetic valve device that includes a mechanism for fine tuning the positions of the valve relative to the frame that seats the valve. It also is an object of the invention to provide a percutaneous valve device that is minimally invasive during delivery and comprises a mechanism by which the position of the valve relative to the frame may be finely adjusted. Another object of the invention is to provide a method of percutaneous delivery of a percutaneous valve device, that includes an iterative feedback process for adjusting the position of the device. A further object of the invention is to provide a method of placing a prosthetic valve device percutaneously in a lumen with reasonable accuracy, and subsequently finely adjusting the valve position.

The present invention provides an apparatus and method to finely adjust the position of the valve member of a percutaneous prosthetic valve device. The apparatus for adjusting the position of the valve member is an adjustment mechanism. The adjustment mechanism according to the present invention includes a means for adjusting the axial position of the valve member (i.e., the position along the longitudinal axis of the device) and/or a means for adjusting the angular position of the valve member relative to the device frame. The adjustment mechanism of the invention may also comprise a position-maintaining means, similar to a locking mechanism.

The adjustment mechanisms of the invention permit a relative range of motion between the valve member and the device frame of the prosthetic valve device, and therefore allow for optimization of the valve member's axial and/or angular position after and/or during implantation. For example, where the device frame is anchored to the native vessel/tissue, axial adjustment of the valve member relative to the device frame also provides axial adjustment of the valve member relative to the native vessel/tissue. The adjustment mechanism of the invention may include a first structure located on the valve member and a second structure on the device frame, which first and second structures make up a complementary configuration pair. The complementary configuration pair permits adjustment of the position of the valve member relative to the device frame. The first and/or second component of the complementary configuration pair may be an inherent structural feature of the valve member or device frame.

The present invention is applicable to both a modular prosthetic valve device, which comprises a plurality of device modules that are delivered and then assembled in vivo, and a pre-assembled percutaneous valve device. For example, pre-assembled percutaneous valves may be manufactured to include the adjustment mechanisms of the present invention, so that after delivery the valve member may be adjusted relative to the device frame.

Advantages that may be achieved by means of the present invention include the ability to finely and more accurately adjust the position of the valve device. Another advantage of the present invention is the ability to initially implant the percutaneous valve device with slightly less accuracy and thereby quickly regain valve function, because the adjustment mechanism permits post-implantation fine-tuning of the position of the valve. Another advantage of the present invention, when used with a modular valve device, is that the reduced bulkiness of the modular valve device permits use of a smaller delivery device and increases flexibility of the loaded delivery device.

DETAILED DESCRIPTION OF THE INVENTION

Figure 1A:
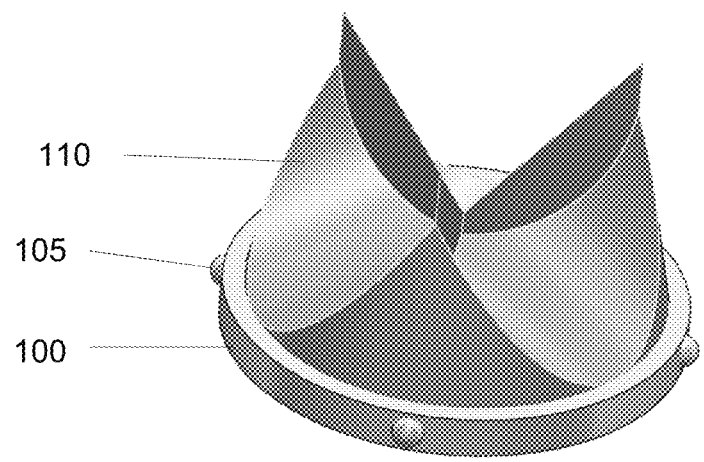
FIGS. 1A-1B illustrate a quick-release mechanism for adjusting and locking a valve module to a support structure.

The present invention provides an adjustment mechanism for performing fine adjustment to the position of the valve member of a prosthetic valve device, a prosthetic valve device that includes such an adjustment mechanism, and a method of adjusting the position of a valve member of a prosthetic valve device. In particular, the present invention provides an adjustment mechanism for either a modular percutaneous prosthetic valve device or a pre-assembled percutaneous valve device. The adjustment mechanism of the invention permits the operator to finely position the valve member of the percutaneous valve device after implantation of the valve device, by moving the valve member in fine increments axially and/or angularly relative to the device frame (for example a support structure of a modular percutaneous valve device or the frame of a pre-assembled percutaneous valve device), and relative to the native vessel in which the device frame has been implanted. By "valve member" is meant the portion of the prosthetic valve device that includes leaflets which open and close to permit one-way fluid flow, similar to the action of a normally functioning native valve, and in many cases a definable inlet end and outlet end. By "device frame" is meant the portion of the prosthetic valve device that functions to seat the valve member at the implantation site and anchor it there. The invention further provides a system for improved positioning of a valve member in a body lumen and a method for facilitating accurate positioning of the valve member in the body lumen.

The present invention may include a means for selectively maintaining the position of the valve member relative to the device frame, as well as resetting the position, e.g., by appropriate application of force in a particular direction. The invention further encompasses methods of adjusting the position of a valve member relative to a device frame after delivering a prosthetic valve to a body lumen in need thereof.

The adjustment mechanism according to the present invention encompasses a means for adjusting the position of the valve member in an axial direction and/or a means for adjusting the position of the valve member in an angular direction. In general terms, the adjustment mechanism of the invention comprises a complementary configuration pair that includes on the valve member a first structure having a first configuration and on the device frame a structure having a second configuration. The device frame, which seats the valve member at the implantation site, may be, e.g., a support structure of a modular valve device. The first and second structures have complementary configurations because they preferably fit together to allow controlled relative motion between the valve member and the device frame. For example, in one embodiment, the complementary configuration pair comprises a helical rail and a roller that fits on the rail. In another embodiment, the complementary configuration pair may be a angular ridges and angular grooves.

In some embodiments, the adjustment mechanism may include a position-maintaining means. In general, the position-maintaining means is a physical or magnetic force that only allows the device's position to be advanced upon application of a proper amount and direction of force, such as arrangements where a pin or ridge fits into any one of a plurality of variously or serially positioned slots or ratchet-type configurations. For example, button and harbor complementary configuration pair may be designed so that the button is spring-loaded such that a threshold amount of force against the button is required to push the button out of the harbor. In another embodiment, the complementary pair configuration may be designed in a manner that allows advancement of the valve member relative to the device frame upon application of a threshold amount of force in a particular direction, similar to a ratchet mechanism.

The devices, systems and methods are particularly adapted for use in percutaneous aortic valve replacement, but may also find use as replacements for other cardiac valves, such as, e.g., pulmonic, mitral and tricuspid valves, as well as valves in the peripheral vasculature or in other bodily lumens, such as the alimentary canal, e.g., esophagus; lymph ducts; the biliary duct; and any other lumens having valves requiring replacement or needing valve implantation. Where the percutaneous valve device is a modular valve device designed to replace an aortic valve, it may be assembled for example in the ascending aorta, the descending aorta, the left ventricle, at the implantation site, or part at the implantation site and part in the aorta. Although particularly adapted for use in lumens of the human body, the devices, systems and methods may also find application in animals.

The aforementioned embodiments, as well as other embodiments, delivery methods, different designs and different types of devices are discussed and explained below with reference to the accompanying drawings. Note that the drawings are provided as an exemplary understanding of the present invention and to schematically illustrate particular embodiments of the present invention. The skilled person will readily recognize other similar examples equally within the scope of the invention. The drawings are not intended to limit the scope of the present invention defined in the appended claims.

The adjustment mechanism permits fine adjustment of the position of the valve member relative to the device frame of the prosthetic valve device by a variety of means. Exemplary embodiments of adjustment mechanisms within the scope of the invention are illustrated in FIGS. 1-7 with reference to modular percutaneous valve devices that are delivered in parts and assembled in the body. However, the invention may also be applied to non-modular, pre-assembled prosthetic valve devices. Modular valve devices are described in detail in ¶¶29-30, 32-34, 39-49 and FIGS. 1-4c of priority U.S. provisional application No. 61/144,007, in ¶¶37-47, 60-62, 65-82 and FIGS. 1-6c of co-pending U.S. patent application Ser. No. 12/686,335 (modular), entitled "Modular Percutaneous Valve Structure and Delivery Method", filed on date even herewith, and in ¶¶43, 48-57 and FIGS. 1-4b of co-pending U.S. patent application Ser. No. 12/686, 338 (self-assembly), entitled "Self-Assembling Modular Percutaneous Valve and Methods of Folding, Assembly and Delivery," filed on date even herewith, which applications are incorporated herein by reference. Briefly, the modular valve device comprises a plurality of device modules for delivery. For example, the plurality of device modules may include a valve module and a support structure, which are designed to be assembled in the body. The valve module is the portion of the valve device having leaflets and once assembled provides a conduit having a inlet end and an outlet end. The valve module may itself comprise a plurality of device modules. Thus, in one embodiment, the valve module may further comprise a plurality of valve sections, which may be assembled in vivo to form a valve assembly. A valve assembly of the modular valve device is the equivalent of the valve member in accordance with the present invention. The support structure provides the framework, or backbone, of the device, housing the valve module and holding the valve module in place within the body. A support structure of the modular valve device is the equivalent of the device frame in accordance with the present invention.

Figure 1B:
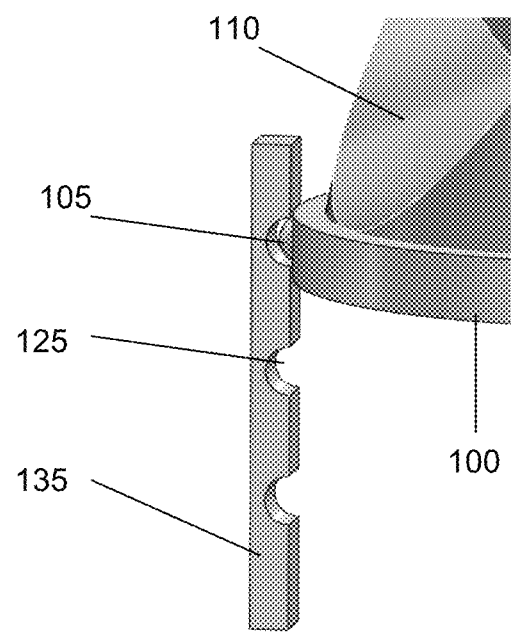

In an embodiment of the present invention illustrated in FIGS. 1A and 1B, the adjustment mechanism comprises a quick-release button locking mechanism comprising "buttons" 105 or "bumps" as a first structure in conjunction with complementary "harbors" 125 as a second structure. As shown in FIG. 1A, the valve member 110 may be attached to or comprise a ring 100. The ring 100 includes a plurality of "buttons" 105 or "bumps" located on its outer surface at defined intervals around the circumference of the ring 100. The device frame (not shown, for clarity) comprises a plurality of posts 135 attached to it on its interior surface and oriented in an axial direction, as shown in FIG. 1B. The plurality of posts 135 are attached to the device frame at defined intervals around the inner circumference that match up with the buttons 105 on the ring 100. Each post 135 includes on an interior surface a plurality of "harbors" 125 (for example, cut-out grooves). The ring 100 may be locked to harbors 125 on a post 135 attached to a device frame (not shown) via the buttons 105 that comprise a quick release mechanism, allowing adjustment of the position of the valve member relative to the device frame along the longitudinal axis of the valve device, e.g., along the aortic root axis, where the aortic valve is to be replaced.

In one aspect of this embodiment, pulling or pushing a safety catch may activate or deactivate the quick release mechanism. For example, upon activation of the safety catch, the buttons 105 are activated such that they protrude outwardly from the outer surface of the ring 100, thereby locking into the harbors 125 of the post 135. Similarly, upon deactivation of the safety catch, the buttons 105 are deactivated such that they retract from the harbors 125 to appear substantially even with the outer surface of the ring 100, thereby unlocking the valve member from the device frame. In an alternative aspect of the invention, the buttons 105 are spring loaded and activate and deactivate according to whether the spring is engaged or disengaged. As illustrated by one button 105 and a plurality of harbors 125 on one post 135 in FIG. 1B, the ring 100 may be docked in any one of several sets of harbors 125 on the plurality of posts 135 attached to the device frame, allowing adjustments along the aortic root axis. Preferably the harbors 125 are spaced apart by about 0.5-3 mm. In the embodiment illustrated in FIGS. 1A and 1B, the valve device comprises four pairs of first and second structures, however in other embodiments, the valve device may have three pairs or as many as six or eight pairs of first and second structures.

Figure 2:
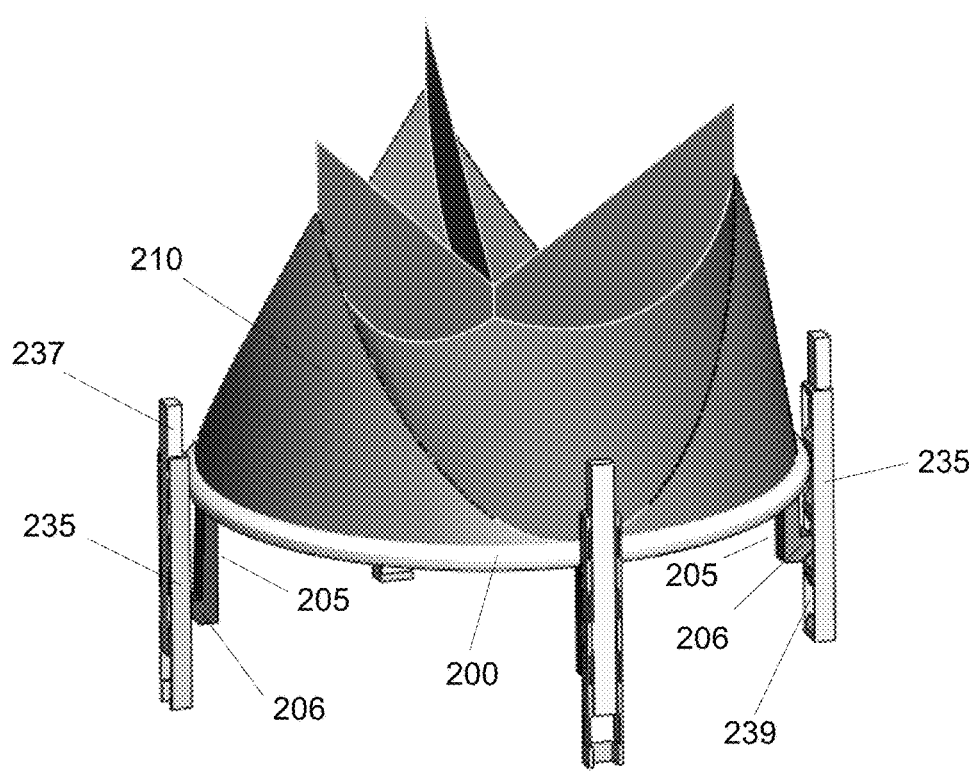
FIG. 2 illustrates a controlled snap-fit mechanism for adjusting and locking a valve module to a support structure.

As illustrated in another embodiment of the invention depicted in FIG. 2, the adjustment mechanism may comprise a controlled snap-fit locking mechanism comprising snap-fit pads 205 as a first structure in conjunction with posts 235 having complementary openings 239 as a second structure. In this embodiment, the valve member 210 is attached to or comprises a ring 200. The ring 200 includes several snap-fit pads 205 mounted underneath the ring 200 at defined intervals around the circumference of the ring 200. The device frame (not shown, for clarity) comprises a plurality of posts 235 attached to it on its interior surface and oriented in an axial direction. The plurality of posts 235 are attached to the device frame at defined intervals around the inner circumference that match up with the snap-fit pads 205 on the ring 200. Each post 235 includes a plurality of openings 239 on its interior surface and a safety slide 237 for locking a snap-fit pad 205 into an opening 239 of the post 235. Preferably the openings 239 are spaced apart by about 0.5-3 mm. Each of the snap-fit pads 205 includes an angular head 206 for insertion into an opening 239 of a post 235. Upon release of the safety slide 237, the valve member 210 may be adjusted until a snap-fit pad 205 engages a desired opening 239. The snap-fit pad 205 then may be locked into the opening 239 of the post 235 via the angular head 206 and the safety slide 237.

In one aspect of this embodiment, the snap-fit pad 205 may be spring-loaded and may be locked into an opening 239 of the post 235 after the angular head 206 of the snap-fit pad 205 engages an opening 239, by depressing the safety slide 237 to allow it to move proximally. The new more proximal position of the safety slide 237 partially unblocks the opening 239, thereby locking the angular head 206 of the snap-fit pad 205 into the opening 239. In another embodiment, the snap-fit pad 205 may be unlocked from an opening 239 of a post 235 by a reverse method, i.e., by moving the safety slide 237 distally to unblock the opening 239 and permit the angular head 206 to disengage from the opening 239. In still another embodiment, the safety slide 237 may be moved either proximally or distally to unblock the opening 239. The safety slide 237 may be moved using pull wires or push-rods. In the embodiment illustrated in FIG. 2, the valve device comprises four pairs of first and second structures, however in other embodiments, the valve device may have three pairs or as many as six or eight pairs of first and second structures. The valve ring may be moved axially along the aortic root until a satisfactory location is achieved.

Figure 3A:
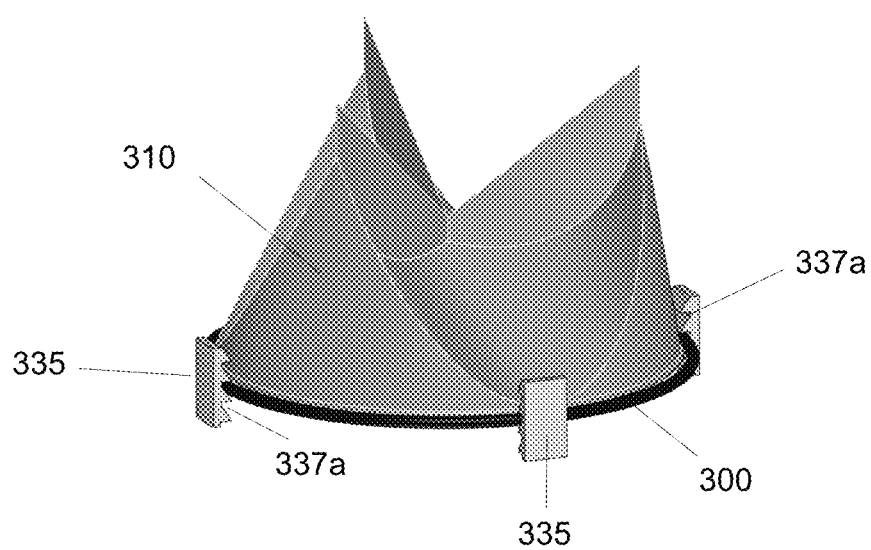
FIGS. 3A-3B illustrate a ratchet positioning mechanism for adjusting and locking a valve module to a support structure.
Figure 3B:
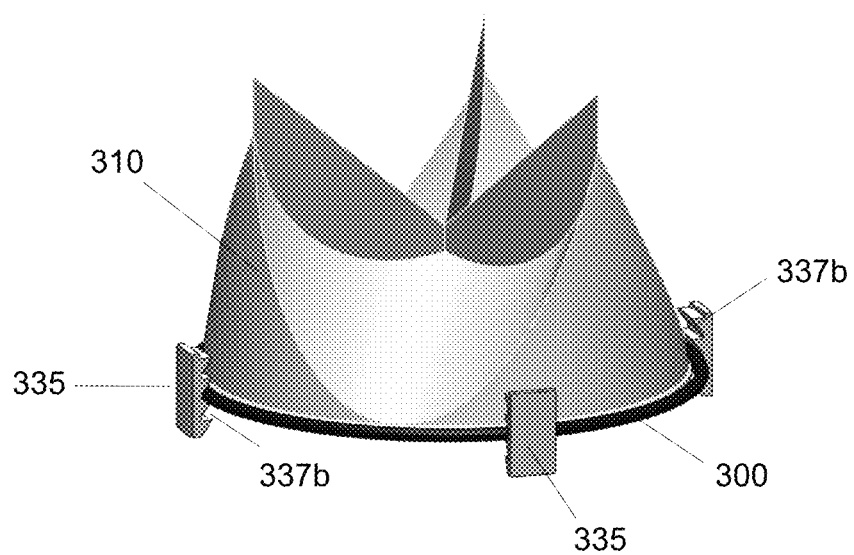

In still yet another embodiment of the invention illustrated in FIGS. 3A and 3B, the adjustment mechanism comprises a ratchet mechanism comprising a valve member 310 attached to or comprising a ring 300 as a first structure in conjunction with posts having complementary ratchets—a ratchet post 335—as a second structure. The device frame (not shown, for clarity) comprises a plurality of ratchet posts 335 attached to it on its interior surface and oriented in an axial direction. The plurality of ratchet posts 335 are attached to the device frame at defined intervals around the inner circumference. The ratchet posts 335 include a plurality of grooves 337. Preferably the grooves 337 are spaced apart by about 0.5-3 mm. As illustrated in FIG. 3A, the grooves 337a may be angled distally (e.g., away from the aorta) or, as depicted in FIG. 3B, the grooves 337b may be angled proximally (e.g., toward the aorta). The grooves 337 operate to lock the ring 300, and therefore the valve member 310, at a particular position relative to the device frame. The ring 300 may be constricted to a relatively small radius to allow easier movement and fine tuning. In the embodiment illustrated in FIGS. 3A-3B, the valve device comprises four pairs of first and second structures, however in other embodiments, the valve device may have three pairs or as many as six or eight pairs of first and second structures. The leaflet ring is moved axially along the aortic root until a satisfactory location is achieved.

Figure 4A:
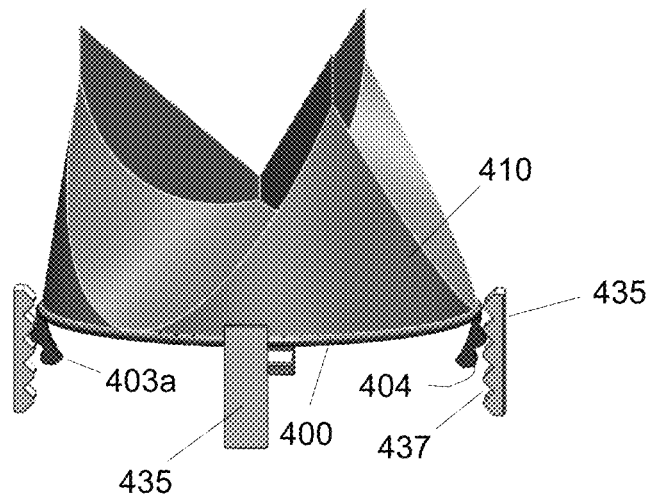
FIGS. 4A-4C illustrate a snap rivet mechanism for adjusting and locking a valve module to a support structure.
Figure 4B:
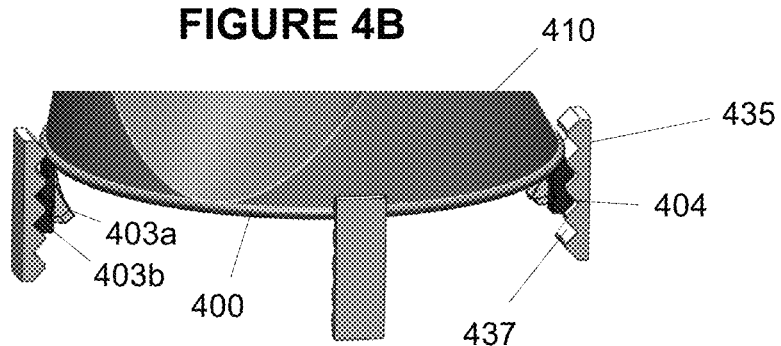
Figure 4C:
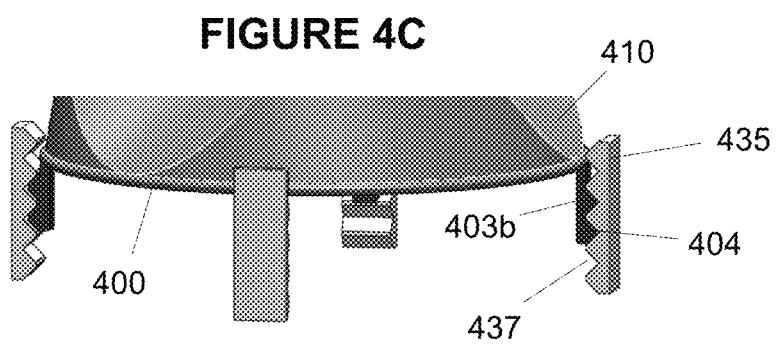

As depicted in another embodiment of the invention illustrated in FIGS. 4A-4C, the adjustment mechanism comprises a snap-rivet locking mechanism comprising flexible pads 403 having at least one angular rib 404 as a first structure in conjunction with posts 435 having a plurality of complementary angular grooves 437 as a second structure. The valve member 410 is attached to or comprises a ring 400. The ring 400 includes a plurality of flexible pads 403 attached thereto. Each of the flexible pads 403 includes at least one angular rib 404 that runs perpendicular to the length of the pads. The device frame (not shown, for clarity) comprises a plurality of posts 435 each comprising a plurality of angular grooves 437 for interlocking with the at least one angular rib 404 of the flexible pads 403. Preferably the angular grooves 437 are spaced apart by about 0.5-3 mm. The plurality of posts 435 are attached to the device frame on its interior surface and oriented in an axial direction, and are attached to the device frame at defined intervals around the inner circumference that match up with the flexible pads 403 on the ring 400. In the embodiment illustrated in FIG. 4, the valve device comprises four pairs of first and second structures, however in other embodiments, the valve device may have three pairs or as many as six or eight pairs of first and second structures. The position of the valve member 410 may be adjusted by moving the ring 400 with the flexible pads 403 retracted (retracted flexible pads 403a) in the device frame axially with respect to the aortic root until a satisfactory location is achieved, as shown in FIG. 4A. The flexible pads 403 may then be released, as shown in FIG. 4B, in a manner to allow their angular grooves 437 to be engaged (engaged flexible pads 403b) and interlocked with the angular grooves 437 of the posts 435, as shown in FIG. 4C.

Figure 5:
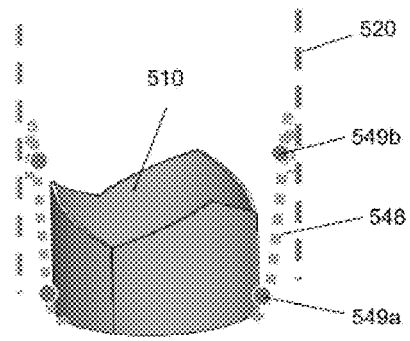
FIG. 5 illustrates a free suspense mechanism for adjusting and locking a valve module to a support structure.

In yet another embodiment of the invention illustrated in FIG. 5, that has particular applicability for a modular valve device, the adjustment mechanism operates separately from a locking mechanism. In this embodiment, a valve assembly 510, for example, may be loosely anchored to the support structure 520, for example to a post of the support structure, via a flexible string 548. The flexible string alternatively may be a net or a flexible wire such as a pull wire, for example. The flexible string 548 may be attached to the valve assembly via a first anchor 549a and may connect the valve assembly 510 to the support structure 520 by looping through the support structure. In one embodiment, a free end of the flexible string may exit the proximal end of the delivery device (i.e., outside the body) that is used to deliver the modular valve. In another embodiment, the non-anchored end of the flexible string may be connected to the delivery device. In this embodiment, mechanisms within the delivery system may assist manipulation of the flexible string 548 to adjust the position of the valve assembly relative to the support structure. Such mechanisms are within the skill in the art. As illustrated in FIG. 5, the flexible string 548 is connected to the first anchor 549a and loops around a hole or string loop (not shown) on the support structure to form a second anchor 549b to loosely suspend the valve assembly 510. By manipulating the free end of the flexible string, the flexible string 548 may be used to finely adjust the position of the valve assembly 510 relative to the support structure 520 before locking the valve assembly to the support structure using a locking mechanism.

Figure 6A:
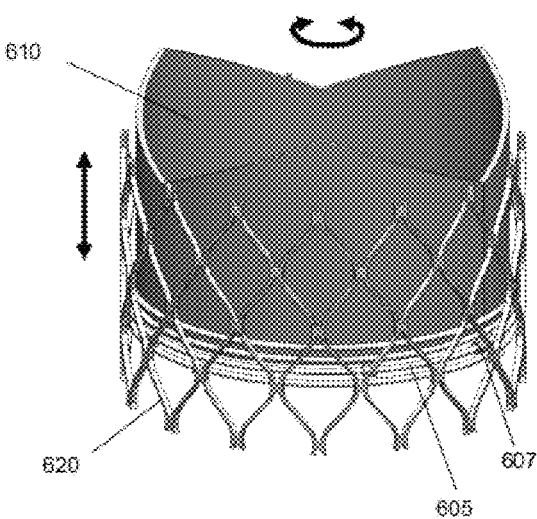
FIG. 6a illustrates a helix rail fine tuning mechanism for adjusting and locking a valve module to a support structure.

FIG. 6a depicts yet another embodiment of the invention in which the position of the valve member 610 may be axially and angularly fine tuned to its optimal location by pushing and pulling it along a helix rail 605. In this embodiment the first structure is a helix rail 605 and the second structure is a roller 607 attached to the device frame 620. As illustrated in FIG. 6a, the helix rail 605 preferably is connected to the valve member, for example a valve component, and the rollers 607 which cooperate with the helix rail 605 are attached to the device frame 620, or support structure. The helix rail 605 and rollers 607 cooperate to permit rotation of the valve member 610 around a longitudinal axis and along one of the "lines" of the helix rail 605, as illustrated. Adjustment of the valve member 610 may be accomplished by pulling or pushing it along the helix rail 605 in a manner that causes the valve member 610 to glide through the rollers 607 in the indicated directions. The valve member may be moved along the helix rail using pull wires or push-rods. The helix rail may be a wire, and in particular may be a shape memory wire. Where the valve device is a modular valve device, the helix rail 605 may be manufactured of a shape memory metal, for example, Nitinol and may be comprised of several interconnected segments. The shape memory helix rail 605 may be delivered in a delivery form that permits a small delivery profile, and then the shape memory helix rail 605 may be triggered to revert to a preconditioned helical coil shape after deployment (as shown in FIG. 6a). For example, the shape memory helix rail 605 may be delivered uncoiled or coiled so as to achieve a smaller delivery diameter than the diameter of the preset helix. The pitch of the preconditioned helical coil shape of the helix rail 605 may be approximately 0.5-2 mm. However, other incremental pitches suitable for the appropriate degree of fine adjustment may also be used. Where used with a modular valve device, the helix rail 605 may be deployed with the valve module (for example a valve component or a series of valve sections) from the delivery system into the support structure for "automatic" subassembly and connection to the rollers 607.

Figure 6B:
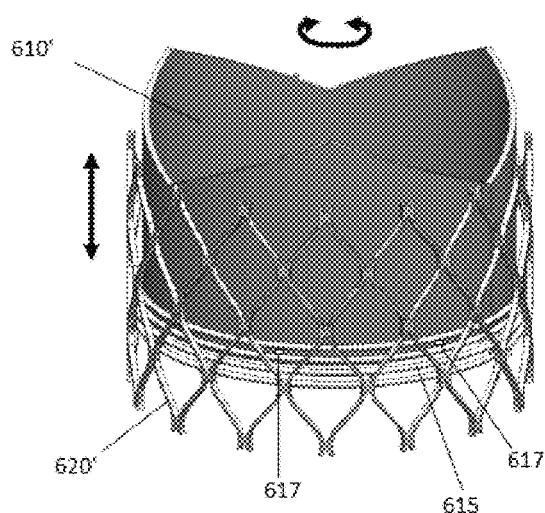
FIG. 6b illustrates a helix groove mechanism for adjusting and locking a valve module to a support structure.

In an alternative of the embodiment of FIG. 6a, the valve member 610' may be axially and angularly fine tuned to its optimal location by pushing and pulling it along a helix groove 615, as depicted in FIG. 6b. In this embodiment, the helix groove 615 may be the second structure on the device frame 620', and the first structure may be a plurality of complementary protrusions 617 located on the valve member 610'. The protrusions 617 may be fixed or spring-loaded for engagement with the helix groove 615.

In most of the above-described embodiments, as is readily recognized by the skilled artisan based on the descriptions herein, the position of the structures designated first and second structures may be reversed. For example, the structure designed a first structure on the valve member may be provided as a second structure on the device frame and the complementary structure designated as a second structure on the device frame may be provided as a first structure on the valve member.

Figure 7:
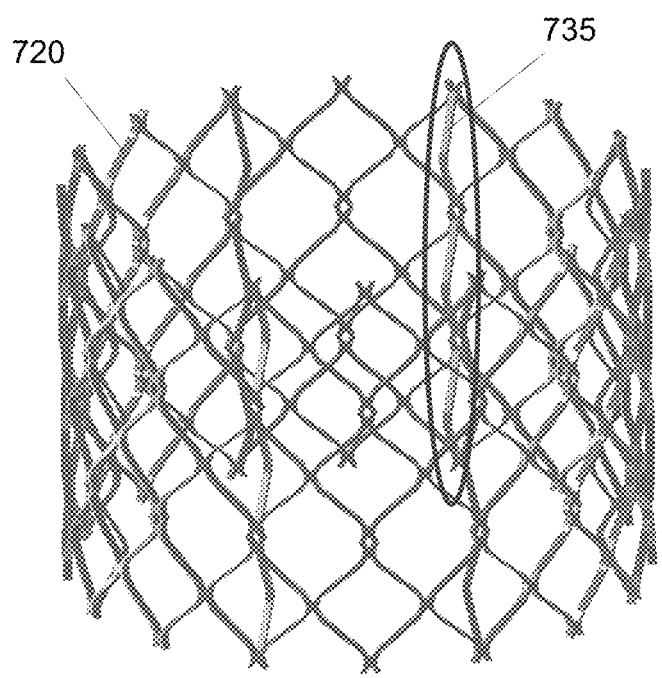
FIG. 7 illustrates an embodiment of posts on a device frame for use with an adjustment mechanism.

As depicted in FIG. 7, a device frame 720 or support structure, which in this embodiment is illustrated as a stent, may include a post 735 as part of a 3-dimensional device frame. FIG. 7 illustrates how a post 735 in accordance with any of the embodiments of FIGS. 1-7 may be attached to a device frame 720 that is a stent without interfering with the expandability of the structure. Preferably the post 735 is sufficiently flexible to not unduly interfere with the axial flexibility of the device frame but sufficiently stiff to function as needed in the particular embodiment in which it is used. Posts 735 may be comprised of the same material as the device frame or a comparable material that does not chemically interact with the material of the device frame. The present invention encompasses substituting the post on the device frame with a groove, where appropriate.

The adjustment mechanisms may be manufactured from metals or non-metals. The base of the valve member, in particular the ring structure, may be made of a metal or a polymer, preferably a deformable polymer. Where the valve device is a modular valve device, the ring structure may be a self-assembly member in its pre-set configuration, as described in ¶¶36-38 and FIGS. 2a-10 of co-pending U.S. application Ser. No. 12/686,338 (self-assembly), filed on date even herewith, which application is incorporated herein by reference.

The adjustment mechanism of the present invention is applicable to all percutaneous prosthetic valve devices, but is particularly useful in conjunction with a modular valve devices. Locking mechanisms may be used to secure or attach together the device frame and valve member, provided the locking mechanism is compatible with the particular adjustment mechanism being used. Examples of locking mechanisms useful in attaching together device modules of a modular valve device are described in ¶¶50-58 and FIGS. 5a-6a of priority U.S. application No. 61/144,007, in ¶¶48-51, 84-113 and FIGS. 7-15 of co-pending U.S. application Ser. No. 12/686,335 (modular), filed on date even herewith, which are incorporated herein by reference. The locking mechanisms preferably are fittings of the kind that are easily engaged from a remote location, yet also provide a secure fitting that will not disengage during use.

The invention also may be applied to pre-assembled percutaneous valve devices. Pre-assembled valve devices are delivered to the affected vessel as one piece, and adjustment of the valve's position is not possible after implantation at the target site. Thus the present invention encompasses incorporating the novel fine adjustment mechanisms into the manufacture of preassembled percutaneous valves, so that the first and second structures having complementary first and second configurations are in place on members of the pre-assembled device prior to delivery (i.e., outside the body). Examples of preassembled, percutaneous prosthetic valves into which the mechanisms of the present invention may be incorporated are described, for example, in U.S. Pat. Nos. 5,411,552 and 6,893,460, and include, for example, the CoreValve Revalving™ System from Medtronic/CoreValve Inc. (Irvine, Calif., USA), Edwards-Sapien or Cribier-Edwards valves from Edwards Lifesciences (Irvine, Calif., USA), and devices in development by, for example, AortTx (Palo Alto, Calif., USA), Sadra Medical, Inc. (Campbell, Calif., USA), Direct Flow Medical (Santa Rosa, Calif., USA), Sorin Group (Saluggia, Italy), and any other variations of prosthetic valves. Previous methods of adjusting the position of the valve involve repositioning the frame—or stent. See U.S. Patent Pub. 2005/0137688 to Salahieh et al; Buellesfeld, L., et al., "Percutaneous Implantation of the First Repositionable Aortic Valve Prosthesis in a Patient With Severe Aortic Stenosis," CATHETERIZATION CARDIOVASCULAR INTERVENTIONS, 71:579-584 (2008); Zegdi, R., et al., "A Repositionable Valve Stent for Endovascular Treatment of Deteriorated Bioprostheses," Journal American College Cardiology, 48:1365-1368 (2006). Such repositioning methods do not permit fine adjustment of the valve position and are less accurate, because one can reasonably expect that any errors in positioning in the first instance are likely to be repeated in subsequent instances. By contrast, the present invention permits fine adjustment of the valve position, in that the valve may be incrementally moved into the correct position, an approach that improves the accuracy of placement by an interative process rather than random placement, as repositioning methods do.

It is important that a prosthetic valve device is placed in a vessel (or lumen) with precision to ensure proper valve function and safety to the patient. Accordingly, the apparatus and method of the invention may be used in conjunction with the placement system and method of placing a modular device, which are described in priority U.S. application No. 61/144,007 at ¶¶67-82 and FIGS. 7a-8, and co-pending US patent application Ser. No. 12/686,337, entitled "A System and Method for Placing a Percutaneous Valve Device," at ¶¶24-42 and FIGS. 1a-2, filed on date even herewith, which applications are incorporated herein by reference.

The embodiments described above are merely illustrative and those of ordinary skill in the art will understand from the teachings herein that a range of mechanisms exists to allow for controlled, relative motion between two structures. For example, other contemplated first and second structures having complementary configurations are: notches at various axial/angular positions along a support structure that allows a valve device to be removably reset among the various positions; hooks/clamps that allow the valve device to be anchored in different locations to a support structure; wires along a support structure that provide a track for, e.g., eyelets on the valve module; or, any other mechanism for causing controlled position adjustment of one structure relative to another.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. An apparatus for adjusting the position of a valve member of a percutaneous valve device, comprising:
a first adjustment structure located on said valve member; and
a second adjustment structure located on a device frame;
wherein said valve member and said device frame together comprise said valve device, wherein said first adjustment structure is configured to fit together with said second adjustment structure in one of a plurality of predetermined positions within a range of relative positions between the valve member and device frame; said apparatus being configured to allow adjustment of one or both of a longitudinal position of said valve member independently of and relative to said device frame and an angular position of said valve member independently of and relative to said device frame.

2. The apparatus of claim 1, wherein the first adjustment structure is a helix rail and the second adjustment structures is a roller.

3. The apparatus of claim 2, wherein the helix rail and roller cooperate to permit rotation of said valve member around a longitudinal axis of the percutaneous valve device.

4. The apparatus of claim 2, wherein said valve member is adapted to permit pushing and pulling thereof along the helix rail.

5. The apparatus of claim 4, further comprising one or both of a pull-wire and a push-rod to affect movement of the valve member.

6. The apparatus of claim 2, wherein the helix rail Is a wire.

7. The apparatus of claim 2, wherein the helix rail Is formed of a shape-memory material.

8. The apparatus of claim 2, wherein the helix rail Is a helical coil.

9. The apparatus of claim 1, wherein the first adjustment structure Is a plurality of complementary protrusions located on said valve member and the second adjustment structure is a helix groove, the protrusions adapted for engagement with the helix groove.

10. The apparatus of claim 9, wherein the protrusions are fixed or spring-loaded.

11. The apparatus of claim 1, wherein said first and second adjustment structures are selected from the group consisting of: buttons and harbors, snap-fit pads and openings, ring and ratchet post, angular ribs and angular grooves, helix rail and rollers, and groove and protrusions.

12. A kit for adjusting the position of a percutaneous valve device, the kit comprising:
a valve member comprising a first adjustment structure; and
a device frame comprising a second adjustment structure, wherein said first adjustment structure Is configured to fit together with said second adjustment structure in one of a plurality of predetermined positions within a range of relative positions between the valve member and device frame;
said kit being configured to allow adjustment of one or both of a longitudinal position of said valve member independently of and relative to said device frame and an angular position of said valve member independently of and relative to said device frame.

13. The kit of claim 12, wherein said valve member and said device frame together comprise said percutaneous valve device.

14. The kit of claim 12, wherein the first adjustment structure is a helix rail and the second adjustment structures is a roller.

15. The kit of claim 12, further comprising one or both of a pull-wire and a push-rod to affect movement of the valve member.

16. The kit of claim 14, wherein the helix rail Is one of a wire and a helical coil.

17. The kit of claim 12, wherein the first adjustment structure is a plurality of complementary protrusions located on said valve member and the second adjustment structure is a helix groove, the protrusions adapted for engagement with the helix groove.

18. The kit of claim 17, wherein the protrusions are fixed or spring-loaded.

19. The kit of claim 12, wherein said first and second adjustment structures are selected from the group consisting of: buttons and harbors, snap-fit pads and openings, ring and ratchet post, angular ribs and angular grooves, helix rail and rollers, and groove and protrusions.

20. The kit of claim 12, further comprising a catheter.

\* \* \* \* \*